(12) United States Patent
Svean et al.

(10) Patent No.: US 6,567,524 B1
(45) Date of Patent: May 20, 2003

(54) NOISE PROTECTION VERIFICATION DEVICE

(75) Inventors: Jarle Svean, Trondheim (NO); Svein Sørsdal, Trondheim (NO); Odd Kr. Ø. Pettersen, Trondheim (NO); Georg E. Ottesen, Trondheim (NO); Sverre Stensby, Trondheim (NO)

(73) Assignee: Nacre AS, Trondheim (NO)

( * ) Notice: Subject to any disclaimer, the term of this patent is extended or adjusted under 35 U.S.C. 154(b) by 214 days.

(21) Appl. No.: 09/653,868

(22) Filed: Sep. 1, 2000

(51) Int. Cl.[7] .................. H04R 25/00; A61F 11/06; G10K 11/16
(52) U.S. Cl. .................. 381/71.1; 381/71.6; 381/72; 381/317; 381/314
(58) Field of Search .................. 381/313, 314, 381/315, 370, 317, 324, 71.6, 312, 316, 318, 320, 319, 322, 323, 71.1, 71.2, 72; 600/25, 559, 23, 24; 623/10

(56) References Cited

U.S. PATENT DOCUMENTS

| | | | | |
|---|---|---|---|---|
| 4,049,930 A | * | 9/1977 | Fletcher et al. | 381/322 |
| 4,489,440 A | * | 12/1984 | Chaoui | 381/71 |
| 4,548,082 A | * | 10/1985 | Engebretson et al. | 128/746 |
| 4,985,925 A | | 1/1991 | Langberg et al. | |
| 5,201,006 A | * | 4/1993 | Weinrich | 381/312 |
| 5,276,739 A | * | 1/1994 | Krokstad et al. | 381/68.2 |
| 5,426,719 A | | 6/1995 | Franks et al. | |
| 5,680,466 A | * | 10/1997 | Zelikovitz | 381/68.1 |

* cited by examiner

Primary Examiner—Rexford Barnie
(74) Attorney, Agent, or Firm—Young & Thompson

(57) ABSTRACT

Ear protecting device with a sealing section for acoustically sealing the meatus of a human, includes a sound generator with a sound outlet for being directed toward the user meatus; an inner microphone with a sound inlet from the meatus, arranged for measuring the resulting sound field in the meatus; connected to an electronics unit including a sound analyser coupled to the inner microphone, for analyzing sound characteristics of the resulting sound field in the meatus, producing analyzed sound characteristics; storing part in the electronics unit for storing measured predetermined sound characteristics of a properly functioning ear protecting device; a comparing part in the electronics unit for comparing the inner microphone analyzed sound characteristics with the stored measured predetermined sound characteristics; indicating part coupled to the comparing part for being activated if the analyzed sound characteristics differ significantly from the predetermined sound characteristics.

14 Claims, 9 Drawing Sheets

NOISE PROTECTION VERIFICATION DEVICE

BACKGROUND OF THE INVENTION

The invention concerns the physical design of an adaptive hearing protective earplug combined with an audio communications terminal.

DESCRIPTION OF THE RELATED ART

There exist a lot of solutions for hearing protection and audio communication in noisy environments based on earplugs and ear-muffs with earphones (loudspeakers), boom microphones, cheek-bone microphones, or throat microphones. All these solutions have one of more of the following undesirable properties:

heavy and clumsy, uncomfortable, inferior quality of sound pick-up and restoration, poor noise attenuation, attenuate both desired and unwanted sounds.

SUMMARY OF THE INVENTION

It is an object of this invention to provide an ear terminal having none of these shortcomings, being a lightweight, all-in-the-ear intelligent hearing protector with wireless communication. The noise attenuation is automatically adapted to the noise conditions and communication modes. The present invention therefore simultaneously protects the hearing and provides improved communication abilities in different noise environments. It is intended for continuous use during the working day or other periods when hearing protection and/or voice communication is needed.

The invention also concerns a device for utilising the speech sound produced in the ear of a person carrying hearing protective communications ear plugs according to the invention.

Present day devices intended to pick up speech from a person in a very noisy environment represent a technological challenge and take several forts. Common types include A microphone in close proximity to the mouth, carried on a microphone boom. The microphone is made with a characteristic emphasising the near field from the mouth. This type is sometimes referred to as "noise cancelling".

A vibration pickup in contact with the throat, picking up the vibrations of the vocal cord.

The invention concerns the physical design of an adaptive hearing protective earplug combined with an audio communications terminal.

There exist a lot of solutions for hearing protection and audio communication in noisy environments based on earplugs and ear-muffs with earphones (loudspeakers), boom microphones, cheek-bone microphones, or throat microphones. All these solutions have one of more of the following undesirable properties:

heavy and clumsy, uncomfortable, inferior quality of sound pick-up and restoration, poor noise, attenuation, attenuate both desired and unwanted sounds.

It is an object of this invention to provide an ear terminal having none of these shortcomings, being a lightweight, all-in-the-ear intelligent hearing protector with wireless communication. The noise attenuation is automatically adapted to the noise conditions and communication modes. The present invention therefore simultaneously protects the hearing and provides improved communication abilities in different noise environments. It is intended for continuous use during the working day or other periods when hearing protection and/or voice communication is needed.

The invention also concerns a device for utilising the speech sound produced in the ear of a person carrying hearing protective communications ear plugs according to the invention.

Present day devices intended to pick up speech from a person in a very noisy environment represent a technological challenge and take several forms. Common types include A microphone in close proximity to the mouth, carried on a microphone boom. The microphone is made with a characteristic emphasising the near field from the mouth. This type is sometimes referred to as "noise cancelling".

A vibration pickup in contact with the throat, picking up the vibrations of the vocal cord.

A vibration pickup in contact with the wall of the meatus, the outer ear canal, picking up the vibrations of the tissue in the head.

A similar pickup in contact with the cheek-bone.

These device types are either fairly sensitive to acoustic noise masking the speech, or certain speech sounds are poorly transmitted, especially the high frequency consonant sounds necessary for good intelligibility.

Persons exposed to high noise levels are required by health and safety regulations to wear hearing protectors. The protectors take the form either of sealing cups which enclose the ear, or ear plugs which block the ear canal. The latter type of protector is often preferred because of its small size and relatively good comfort.

Thus it is an additional object of this invention to provide an ear plug with two desirable properties:

The cavity sealed off in the inner portion of the meatus by the ear plug is relatively free of external noise, this is the purpose of the ear plug in protecting the hearing.

The sound field in the cavity generated by the persons own voice contains all the frequency components necessary to reconstruct the speech with good intelligibility.

The solution according to invention takes advantage of these facts. By using a microphone to pick up the acoustic sound field in the inner portion of the meatus and processing the microphone signal according to the invention, a speech signal of high quality and low noise masking is produced.

It is an additional object of this invention to provide a system for increasing the user's feeling of naturalness of the user's own voice when using a hearing protective communications terminal according to the invention.

Using ordinary earplugs or earmuffs, the user usually feels his own voice being distorted, a feature reducing the comfort of wearing hearing protectors. Ordinary hearing defenders changes the normal sound transmission path from the mouth to the eardrums. Thus the auditory feedback from the users own voice is affected resulting in an unintended change in the speech output. A normal response is to raise one's own voice level when using headsets or earplugs.

The invention solves this problem by filtering and mixing in the user's own voice picked up by either the outer or the inner microphone at one ear and reproduce the signal at the loudspeaker in the other ear. It is also possible to reproduce the signal by the loudspeaker in the same ear, in which case feedback cancellation has to be applied. Thus the user's voice is felt more natural both with respect to frequency response and speech level. This feature will increase the level of acceptance for continuous use of hearing protectors during the whole working day. The own voice signal is added and reproduced in such a way that the noise reduction property of the hearing protector is maintained.

An additional object of this invention is to provide a programmable personal noise exposure dose meter that measures the true exposure in the user's ear and calculates the hearing damage risk.

Present day noise exposure dose meters, also called dosimeters, usually consist of a microphone and a small electronics unit that may be attached to the body or worn in a pocket. The microphone may be mounted on the electronics unit or it may be fastened to the collar or on the shoulder. ANSI S1.25 specifies dosimeters.

Present day dosimeters have several shortcomings:

Dosimeters do not measure the noise that actually affects the hearing organ (e.g. when the user wears a hearing protector, helmet, etc.). Even when the ear is not covered, measurements may be influenced by body shielding.

Dosimeters are susceptible to non-intentional or intentional errors, which may influence readings, such as wearers tapping or singing into dosimeter microphones or by wind-generated noise.

Dosimeters are inaccurate if impulse or impact noise is present.

The invention solves these problems by using a microphone that measures the sound at the eardrum and employs analysis procedures that take into account both stationary and impulsive sound. When the dose meter is part of a communications terminal this includes external noises, incoming communication signal, as well as possible malfunctioning of the equipment.

It is also an object of this invention to provide a device for verifying in situ that a hearing protector is properly used.

Present day hearing protectors take the form either of sealing cups which enclose the ear, or ear plugs which blocks the ear canal. For both types, it is critically important to avoid leakage of the noise sound through or around the sealing and blocking parts of the hearing protectors.

Experience shows that several factors may compromise the sealing of a hearing protector and thereby increase the risk of hearing damage. These factors include Irregular surfaces which the sealing material is not able to follow properly. Examples are spetacles used with ear cups, and earplugs used by persons with irregularly formed ear canals.

Improper placement of the hearing protector. Experience and patience is required by the user to get a hearing protector mounted correctly. In cases where the user is wearing a helmet or cap, the hearing protector may be accidentally pushed out of position during use.

Ageing of the materials in the sealing may reduce the resilience of the sealing and thereby allow leakage around the sealing.

The result of leakage is reduced damping of potentially harmful noise. Ideally, the leakage should be detected and remedied prior to noise exposure. The leakage may not be clearly audible. Accordingly, noise situations may comprise of intermittent or impulsive components which may damage the hearing almost instantaneously if a hearing protector should be malfunctioning or imperfect without the user's knowledge.

The invention solves these problems by an in situ acoustical measurement, which is analysed and reported to the user in audible form, or to external equipment by means of communication signals. The devices necessary for the measurement are an integral part of the hearing protector. Verification may be activated by the user at any time, or be continuously running when the application is critical. Optionally, verification may be activated by other persons (or devices) than the user, e.g. to verify hearing protector function before admittance to a noisy area is allowed.

The above mentioned problems are solved by the invention according to the attached claims.

BRIEF DESCRIPTION OF THE DRAWINGS

The invention will be described below with reference to the accompanying drawings, the drawings illustrating the invention by way of examples.

DESCRIPTION OF PREFERRED EMBODIMENTS OF THE INVENTION.

The physical design of an embodiment of the present invention enables the construction of a complete all-in-the-ear hearing protector and communications terminal with strong passive sound attenuation, strong active sound attenuation, high quality sound restoration, high quality sound pick-up, small size, low weight, and comfortable fit.

Figure 1:
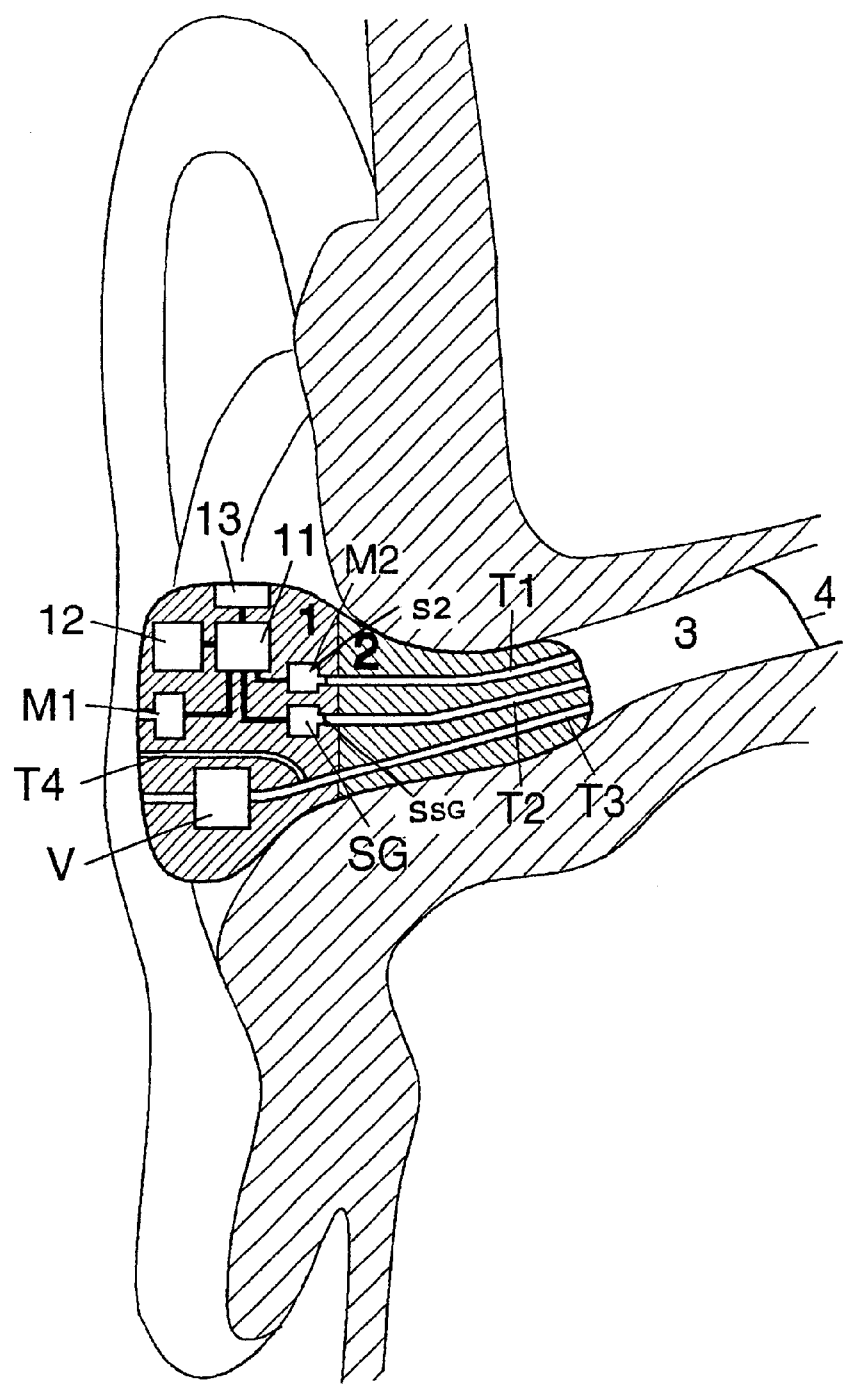
FIG. 1 is a simplified vertical section along the central axis of the meatus of the outer ear of an erect human, with an inserted ear terminal according to one embodiment of the invention also shown in vertical section along the axis, locally coincident with the meatus axis.

One embodiment of this invention is illustrated in FIG. 1, and provides the general physical design of a complete all-in-the-ear hearing protector and communications terminal, regarded as a combination of passive sealing, characteristics and placement of electro-acoustic transducers as well as acoustic filters, electric circuitry, and a ventilation system for pressure equalisation.

The ear terminal comprises an outer section 1 arranged for sitting adjacent to the outward facing portion of the sealing section 2 and a part of the inward facing portion of the outer section 1 is formed to fit the concha around the outer portion of the meatus 3.

The physical design represented by an embodiment of the invention enables some or all of the following functionalities:

External sounds are attenuated by a combination of passive and active noise control. The passive attenuation is obtained by means of an earplug 1,2 with a sealing system 2 inserted in the outer part of the ear canal or meatus 3. The active noise control is achieved by using one or two microphones M1, M2 and a loudspeaker SG together with electronic circuits in an electronics unit 11 mounted in the earplug system. The algoritmes for noise control are per se known and will not be described in any detail here, but may include active noise cancelling by feedback of acoustic signals converted by at least one of said microphones (M1,M2) throught the sound generator (SG).

Restoration of desired sounds (external sounds and signals from the communication system) at the eardrum or tympanum 4 is achieved by using the same microphones M1, M2, and loudspeaker SG and the electronics unit 11. Again, the algoritmes for obtaining this are per se known and will-not be described in any detail here, but may include amplification of chosen frequencies converted by said the microphone (M1) and generating a corresponding acoustic signal through said sound generator (SG). The frequencies may for example be within the normal range of the human voice. Ear terminal according to claim 1, comprising a sound generator (SG) arranged for being directed toward the meatus and being coupled to said electronics unit (11), wherein the electronics unit (11) comprises filtering means for active sound transmission e.g. by amplification of chosen frequencies converted by said outer microphone (M1) and generating a corresponding acoustic signal through said sound generator (SG).

Pick-up of the user's voice is performed by a microphone M2 with access to the closed space in the meatus 3. This signal is processed by means of analogue or digital electronics in the electronics unit 11 to make it highly natural and intelligible, either for the user himself or his communication partners or both parts. This signal is of high quality and well suited for voice control and speech recognition.

Online control and verification of the hearing protector performance is obtained by injecting an acoustic measurement signal, preferably by the sound generator or loudspeaker SG in the meatus, and analysing the signal picked up by the microphone M2 that has access to the acoustic signal in the meatus 3.

Measurement of noise exposure dose at the tympanum 4 and online calculation performed by electronic circuits, and warning of hearing damage risk either by audible or other warning signals, either to the wearer of the hearing protection or other relevant personnel.

Equalisation of pressure between the two sides of the earplug system is obtained by using a very thin duct T3, T4 or a valve that equalises static pressure differences, while retaining strong low frequency sound attenuation. A safety valve V to take care of rapid decompression may be incorporated in the pressure equalisation system T3, T4.

FIG. 1 illustrates an embodiment according to the invention. The earplug comprises a main section 1 containing two microphones M1 and M2 and a sound generator SG. The main section is designed in a way that provides comfortable and secure placement in the concha (the bowl-shaped cavity at the entrance of the ear canal). This may be obtained by using individually moulded ear-pieces that are held in position by the outer ear or by using a flexible surrounding pressing against the structure of the outer ear. A sealing section 2 is attached to the main section The sealing section may be an integral part of the earplug, or it may be interchangeable. The sound inlet of microphone M1 is connected to the outside of the earplug, picking up the external sounds. The microphone M2 is connected to the inner portion of the meatus 3 by means of an acoustic transmission channel T1. The acoustic transmission channel may contain optional additional acoustic filtering elements. An outlet $S_{SG}$ of sound generator SG is open into the inner portion of the meatus 3 by means of an acoustic transmission channel T2 between the sound generator SG and the inward facing portion of the sealing section 2. The acoustic transmission channel T2 may contain optional additional acoustic filtering elements.

When smaller microphones M2, and sound generators SG are available, it will be possible to mount the microphone M2 and the sound generator SG at the innermost part of the sealing section. Then there is no need for the transmission channels T1 and T2.

The two microphones and the sound generator are connected to an electronics unit 11, which may be connected to other equipment by a connection interface 13 that may transmit digital or analogue signals, or both, and optionally power.

Electronics and a power supply 12, e.g. a battery, may be included in main section 1 or in a separate section.

The microphones M1,M2 may in a preferred embodiment be standard miniature electret microphones like the ones used in hearing aids. Recently developed silicon microphones may also be used.

The sound generator SG may in a preferred embodiment be based on the electromagnetic or electrodynamic principle, like sound generators applied in hearing aids.

According to a preferred embodiment of the invention, a safety valve V is incorporated in the ventilation duct comprising the channels T3 and T4. The valve V is arranged to open if the static pressure in the inner part of the meatus 3 exceeds the outside pressure by a predetermined amount, allowing for pressure equalisation during rapid decompression. Such decompression may occur for military or civilian air personnel experiencing rapid loss of external air pressure. Such a decompression may also occur for parachuters, divers, and the like. Pressure equalisation for slowly varying pressure changes is obtained by using a narrow vent T4 which may bypass the valve V. A proper design of this vent T4 allows for static pressure equalisation without sacrificing low-frequency noise attenuation.

The main section of the earplug may be made of standard polymer materials that are used for ordinary hearing aids. The sealing part may be made of a resilient, slowly re-expanding shape retaining polymer foam like PVC, PUR or other materials suitable for earplugs.

For some applications (less extreme noise levels) the earplug may be moulded in one piece 1,2 combining the main section 1 and the sealing section 2. The material for this design may be a typical material used for passive earplugs (Elacin, acryl).

It is also possible to make the earplug in one piece comprising the main section 1 and the sealing section 2, all made of a polymer foam mentioned above, but then the channels T1,T2,T3,T4 have to be made of a wall material preventing the channels T1,T2,T3,T4 to collapse when the sealing section 2 is inserted in the meatus 3.

Figure 2:
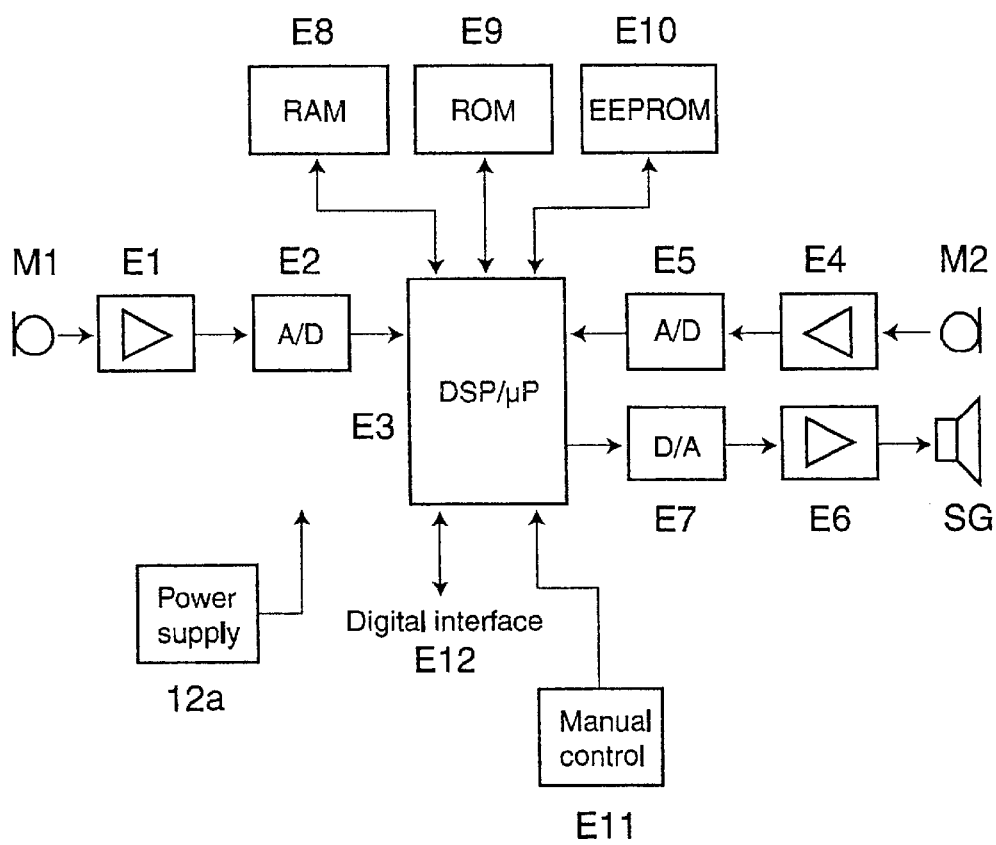
FIG. 2 is an electrical wiring diagram showing the functional components and connections between electronic components in a preferred embodiment according to the invention.

All the features mentioned above may be obtained by an electric circuitry represented by the block diagram in FIG. 2.

The microphone M1 picks up the ambient sound. A signal from the microphone M1 is amplified in E1 and sampled and digitised in an analogue to digital converter E2 and fed to a processing unit E3 that may be a digital signal processor (DSP), a microprocessor (uP) or a combination of both. A signal 51 from microphone M2, which picks up the sound in the meatus 3 between the isolating section 2 and the tympanum 4, is amplified in the amplifier E4 and sampled and digitised in the analogue to digital converter E5 and fed to the processing unit E3.

A desired digital signal DS is generated in the processing unit E3. This signal DS is converted to analogue form in the digital to analogue converter E7 and fed to the analogue output amplifier E6 that drives the loudspeaker SG. The sound signal produced by the loudspeaker SG is fed to the tympanum 4 via the channel T2 into the meatus 3 as described above.

The processing unit E3 is connected to memory elements RAM (Random access memory) E8, ROM (read only memory) E9, and EEPROM (electrically erasable programmable read only memory) E10. The memories E8,E9, and E10 are in a preferred embodiment of the invention used for storing computer programs, filter coefficients, analysis data and other relevant data.

The electronic circuitry 11 may be connected to other electrical units by a bidirectional digital interface E12. The communication with other electrical units may be performed via a cable or wireless through a digital radio link. The Bluetooth standard for digital short-range radio Specification of the Bluetooth System, Version 1.0 B, Dec. 1, 1999, Telefonaktiebolaget L M Ericsson) is one possible candidate for wireless communication for this digital interface E12.

In a preferred embodiment of the invention, signals that may be transmitted through this interface are:
program code for the processing unit E3 analysis data from the processing unit E3 synchronisation data when two ear terminals 1,2 are used in a binaural mode
digitised audio signals in both directions to and from an ear terminal 1,2.
control signals for controlling the operation of the ear terminal.
digital measurement signals for diagnosis of the ear terminal performance.

A manual control signal may be generated in E11 and fed to the processing unit E3. The control signal may be generated by operating buttons, switches, etc, and may be used to turn the unit on and off, to change operation mode, etc. In an alternative embodiment, a predetermined voice signal may constitute control signals to the processing unit E3.

The electric circuitry is powered by the power supply 12a that may be a primary or rechargeable battery arranged in the earplug or in a separate unit, or it may be powered via a connection to another equipment, e.g. a communication radio.

One embodiment of the invention concerns the use of the ear terminal as an "in-the-ear voice pick-up". The sound of a person's own voice as heard in the meatus is not identical to the sound of the same person's voice as heard by an external listener. The present embodiment of the invention remedies this problem. The microphone M2 illustrated in FIG. 3 picks up the sound in the inner portion of the meatus 3 sealed off by a sealing section 2 in an ear protecting communications device of the earplug type. The signal is amplified by the amplifier E4 illustrated in FIGS. 2, A/D converted by the A/D converter E5, and processed in the digital signal processing (DSP) or microcomputer unit E3. The processing may be viewed as a signal dependent filtering taking into account the speech signal properties as well as computed estimates of the location of sound generation for the different speech sounds. Thereby the speech intelligibility and naturalness may be improved.

Figure 3:
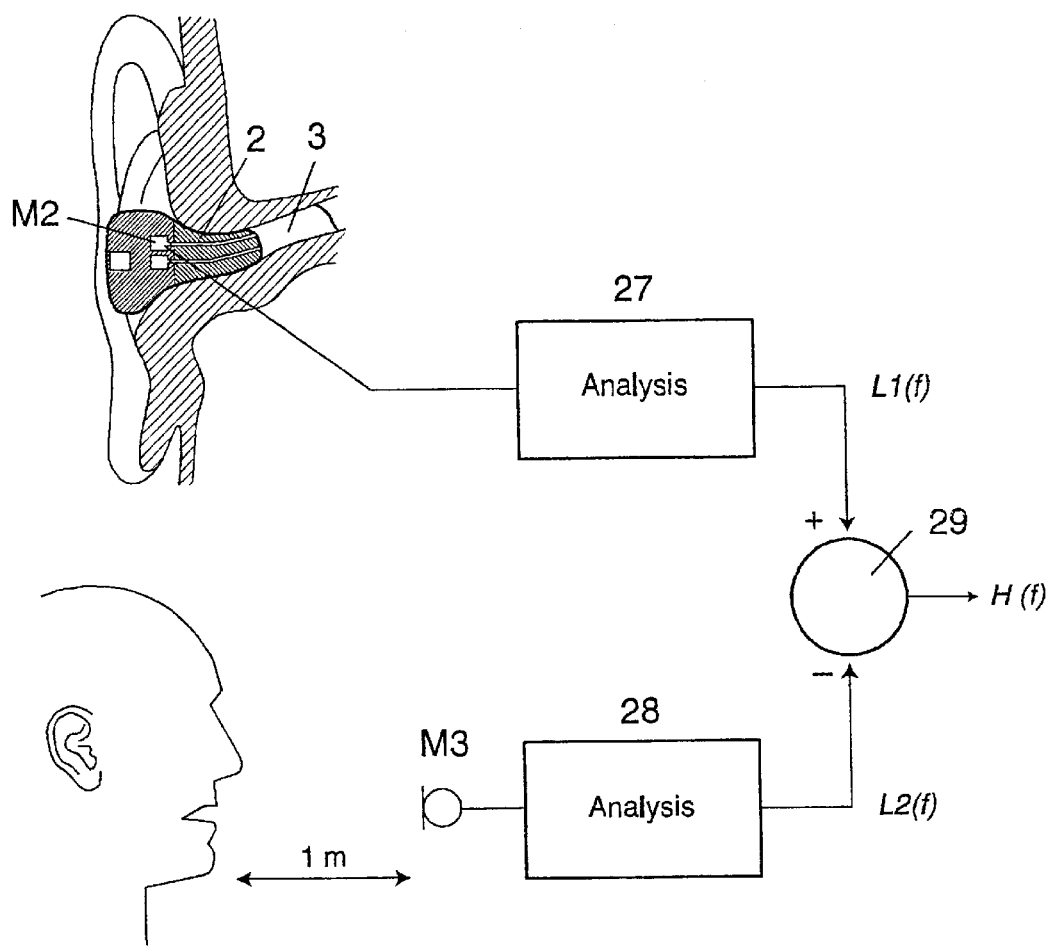
FIG. 3 is an illustration of one method according to the invention, showing that spectral analysis of sound picked up in the ear is compared with spectral analysis of sound picked up by a microphone at a standard distance, e.g. of 1 metre, under otherwise quiet conditions.

FIGS. 1 and 3 show examples of embodiments of the invention, with the microphone M2 being integrated in a hearing protective communications earplug. The acoustic transmission channel T1 connects microphone M2 to the inner portion of the meatus 3. Microphone M2 picks up the sound field produced by the person's own voice. The signal may be amplified in amplifier E4, A/D converted in A/D converter E5 and processed in the digital signal processing (DSP) or microcomputer unit E3. A processed signal from E3 may be transmitted in digital form through a digital interface E12 to other electrical units. In an alternative embodiment, the processed signal from E3 may be D/A converted and transmitted in analogue form to other electrical units.

Figure 4:
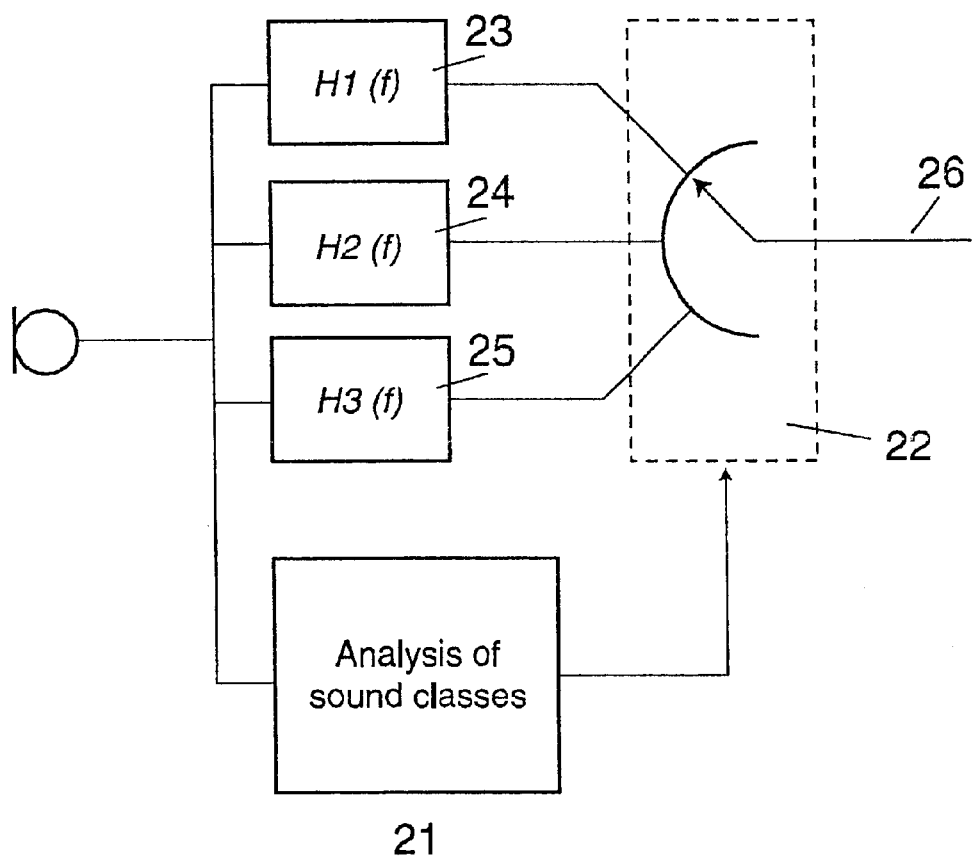
FIG. 4 is an illustration of speech sound analysis and following sound source classification with filtering conducted according to the sound source classification, according to one embodiment of the invention.

FIG. 4 illustrates one possible signal processing arrangement according to the invention. It illustrates an example of the type of signal dependent filtering which may be applied to the signal from microphone M2 in order to obtain a good reconstruction of the speech signal, making it highly intelligible, even in extremely noisy environments.

After amplification in E4 and A/D-conversion E5, the microphone M2 signal is analysed in the DSP/uP processing unit E3. The analysis represented by block 21 in FIG. 4 may comprise a short term estimate of the spectral power in the microphone signal, a short term auto-correlation estimate of the microphone signal, or a combination of both. Based on these estimates, a running classification with corresponding decision represented by block 22 may be made in the processing unit E3 for the selection of the most suitable conditioning filter for the signal from microphone M2. In the example shown in FIG. 4, the selection may made between e.g. three filters H1(f), H2(f) and H3(f) represented by blocks 23, 24 and 25, appropriate for vowel sounds, nasal sounds and fricative sounds respectively. The processed signal is present at output 26 of block 22. Other sound classifications using more sophisticated subdivisions between sound classifications and corresponding sound filters and analysis algorithms may be applied. The selection algorithm may comprise gradual transitions between the filter outputs in order to avoid audible artefacts. Filtering and selection is carried out in the processing unit E3 concurrently with the sound analysis and classification.

The basis for the filter characteristics and the corresponding analysis and classification in the processing unit E3 may be derived from an experiment of the form shown in FIG. 3. An ear plug with a microphone M2 with the same properties as the one used for the voice pickup is used to pick up the voice of a test subject from the meatus 3 illustrated in the upper part of FIG. 3. Concurrently, the voice is recorded by a high quality microphone M3 in front of the subject, at a nominal distance of 1 meter, under an-echoic conditions. Estimates of the power spectral densities may be computed for the two signals by the analyses represented by blocks 27 and 28 respectively, and the corresponding levels L1(f) and L2(f) are compared in comparator 29. The output from the comparator is represented by the transfer function H(f). The analyses may be short time spectral estimates, e.g. ⅓ octave spectra in the frequency range 100 Hz to 14000 Hz. The test sequences which the subject utters may comprise speech sounds held constant for approximately 1 second. For voiced sounds, the subject person may make the pitch vary during the analysis period. The transfer functions of the filters described in connection with FIG. 4 may be based on diagrams of H(f), the spectral density levels of the free field microphone M3 subtracted from the corresponding levels of the in-the-ear microphone M2.

A simplest embodiment of the invention may reduce the system in FIG. 4 to one single time invariant filter. The analysis and selection processing may then be omitted. The transfer function of the single filter is still based on diagrams of the spectral density levels of the free field microphone subtracted from the corresponding levels of the in-the-ear microphone, described in connection with FIG. 3. The transfer function may be a combination of the results for the various speech sounds, weighted in accordance with their importance for the intelligibility and naturalness of the processed speech.

Another embodiment of the invention is best understood under the term "Natural Own Voice", indicating that a person wearing an ear terminal shall perceive his own voice as being natural while having the meatus blocked by an earplug.

The inner microphone M2 or the outer microphone M1, or a combination of both, picks up the sound signal representing the users voice signal. The signal is amplified, A/D converted, and analysed in the digital signal processor E3. Based on previously measured transfer functions from the user's speech to the microphone M2 (and/or M1), the microphone signal may be filtered to regain the naturalness of the user's speech. The signal is then D/A-converted, amplified and reproduced at an internal loudspeaker SG. The internal loudspeaker SG may be arranged in a similar ear terminal 1,2 in the wearer's other ear to prevent local feedback in the earplug. In a more acoustically demanding arrangement the loudspeaker SG, arranged in the same meatus 3 as the inner pickup microphone M2 is situated, may be used, thus demanding feedback cancellation. The desired signal to the loudspeaker SG in the other ear may be transmitted via electric conductors outside of the wearer's head, or via radio signals.

Figure 6:
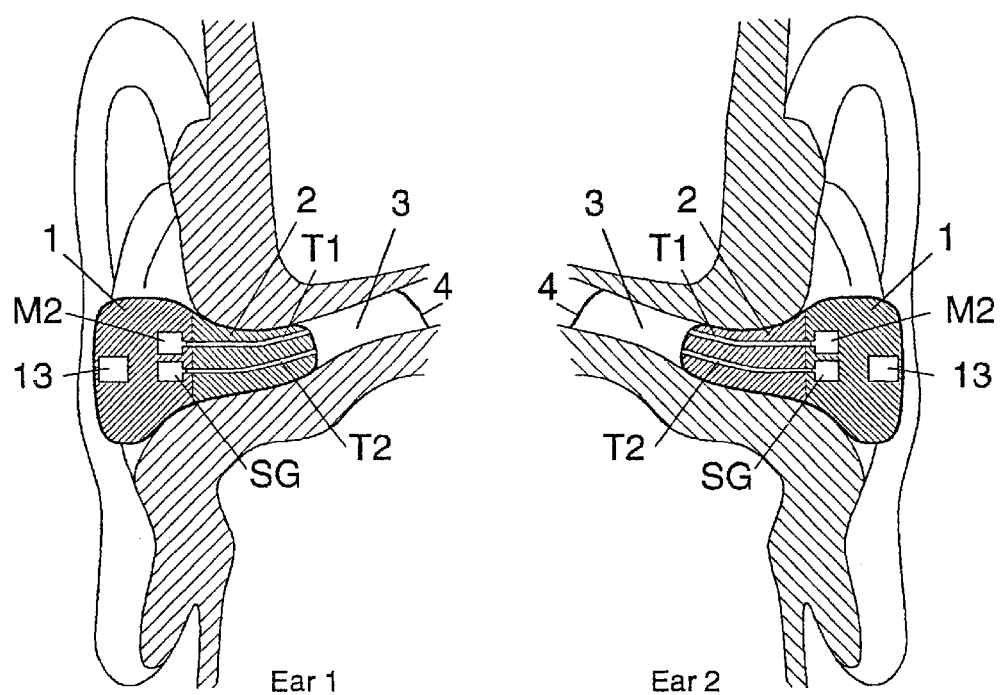
FIG. 6 illustrates a simplified section through a human's right and left ears with ear terminals according to the invention illustrated for improved natural sound purposes.

FIG. 6 shows one preferred embodiment of the invention with the natural own voice feature being integrated in two active hearing protective communications earplugs. Each earplug may comprise a main section 1 containing two microphones, an outer microphone M1 and an inner microphone M2, and a sound generator SG. The right and left earplugs are generally symmetrical, otherwise identical for both ears. Section 2 is the acoustic sealing of the hearing protector. An acoustic transmission channel T1 connects microphone M2 to the inner portion of meatus 3. Microphone M2 picks up the sound from the meatus 3. When the user is speaking and the ear canal is sealed, this signal is mainly the user's own voice signal. This is filtered and reproduced at the loudspeaker SG at the other ear. An acoustic transmission channel T2 connects sound generator SG to the inner portion of meatus 3. A block diagram of the electronic system is shown in FIG. 2.

FIG. 4 shows an example of the type of signal dependent filtering which may be applied to the microphone signal in order to obtain a good reconstruction of the voice.

After amplification in E4 and A/D-conversion E5, the microphone M2 signal is analysed in the DSP/uP processing unit E3. The analysis represented by block 21 in FIG. 4 may comprise a short term estimate of the spectral power in the microphone signal, a short term auto-correlation estimate of the microphone signal, or a combination of both. Based on these estimates, a running classification with corresponding decision represented by block 22 may be made in the processing unit E3 for the selection of the most suitable conditioning filter for the signal from microphone M2. In the example shown in FIG. 4, the selection may made between e.g. three filters H1(f), H2(f) and H3(f) represented by blocks 23, 24 and 25, appropriate for vowel sounds, nasal sounds and fricative sounds respectively. The processed signal is present at output 26 of block 22. Other sound classifications using more sophisticated subdivisions between sound classifications and corresponding sound filters and analysis algorithms may be applied. The selection algorithm may comprise gradual transitions between the filter outputs in order to avoid audible artefacts. Filtering and selection is carried out in the processing unit E3 concurrently with the sound analysis and classification.

Figure 5:
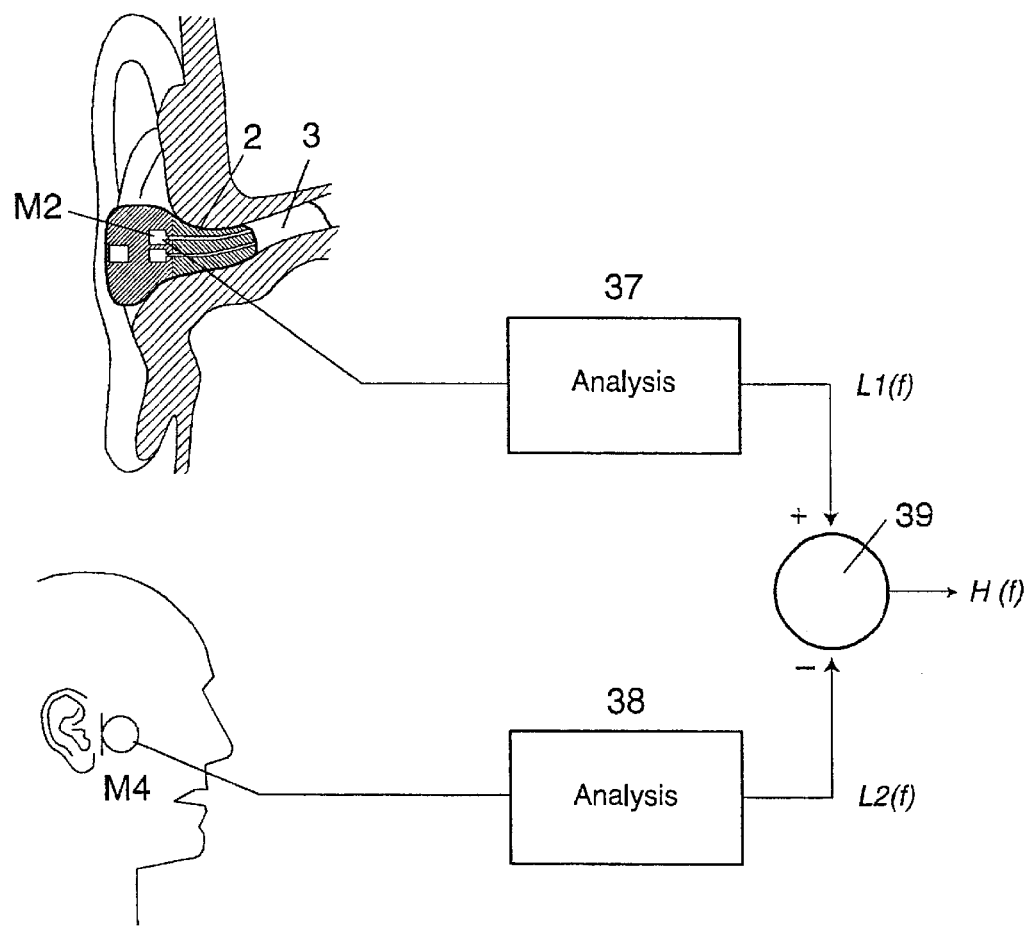
FIG. 5 is an illustration of another method according to the invention, illustrating an analysis of sound picked up close to the ear being compared with an analysis of sound picked up by a microphone arranged in the meatus.

The basis for the filter characteristics and the corresponding analysis and classification in the processing unit E3 may be derived from an experiment of the form shown in FIG. 5. An ear plug with a microphone M2 with generally the same properties as the one used for the voice pickup is used to pick up the voice of a test subject from the meatus 3 illustrated in the upper part of FIG. 5. Concurrently, the voice is recorded by a high quality microphone M4 close to the subject's ear, under an-echoic conditions. Estimates of the power spectral densities may be computed for the two signals by the analyses represented by blocks 37 and 38 respectively, and the corresponding levels L1(f) and L2(f) are compared in comparator 39. The output from the comparator is represented by the transfer function H(f). The analyses may be short time spectral estimates, e.g. ⅓ octave spectra in the frequency range 100 Hz to 14000 Hz. The test sequences which the subject utters may comprise speech sounds held constant for approximately 1 second. For voiced sounds, the subject may make the pitch vary during the analysis period. The transfer functions of the filters described in connection with FIG. 4 may be based on diagrams of H(f), the spectral density levels of the free field microphone M4 subtracted from the corresponding levels of the in-the-ear microphone M2.

A simplest embodiment of the intention may reduce the system in FIG. 4 to one single time invariant filter. The analysis and selection processing may then be omitted. The transfer function of the single filter is still based on diagrams of the spectral density levels of the free field microphone subtracted from the corresponding levels of the in-the-ear microphone, described in connection with FIG. 5. The transfer function may be a combination of the results for the various speech sounds, weighted in accordance with their importance for the naturalness of the processed speech.

Another embodiment of the invention is called a "Personal Noise Exposure Dose Meter". Similar to the above embodiments, a microphone M2 picks up the sound in the meatus 3. One of the novel features is that this noise exposure is measured in the meatus, even while the ear is already noise protected. The signal from the microphone M2 is amplified, A/D converted, and analysed in a digital signal processing (DSP) or microcomputer unit E3 in the same way as described above. According to a preferred embodiment of the invention, the analysis covers both stationary or semistationary noise, and impulsive noise. The result of the analysis is compared to damage risk criteria and the user gets an audible or other form of warning signal when certain limits are about to be exceeded and actions have to be made. The warning signal may also be transmitted to other parties, e.g. industrial health care monitoring devices. The time record of the analysis may according to a preferred embodiment be stored in a memory, e.g. in the RAM E8 for later read-out and processing.

FIG. 1 shows a preferred embodiment of the invention with the personal noise exposure dose meter integrated in an active hearing protective communications earplug, comprising a main section 1 containing two microphones, an outer microphone M1 and an inner microphone M2, and a sound generator SG. Since this embodiment is part of a hearing-protecting earplug, a sealing section 2 is attached to the main section. An acoustic transmission channel T1 connects microphone M2 to the inner portion of the meatus 3. Microphone M2 therefore picks up the sound present in the meatus 3, just outside the eardrum (tympanum) 4. An acoustic transmission channel T2 connects sound generator SG to the inner portion of the meatus 3. The sound generator SG may provide audible information to the user, in form of warning signals or synthetic speech.

All the electronics as well as the battery are provided in the main section 1.

A block diagram of one possible implementation of this embodiment is shown in FIG. 2. The sound is picked up by the microphone M2, amplified, and AD-converted before it is fed to the processing unit E3 with DSP or uP (or both) as central processing units. The memory units E8 with RAM, E9 with ROM, and E10 with EEPROM may store programs, configuration data, and analysis results. Information to the user is generated in the central processing unit E3, DA-converted, amplified, and may be presented as audible information via the loudspeaker SG. The digital interface, is used for programing, control, and readout of results.

Figure 7:
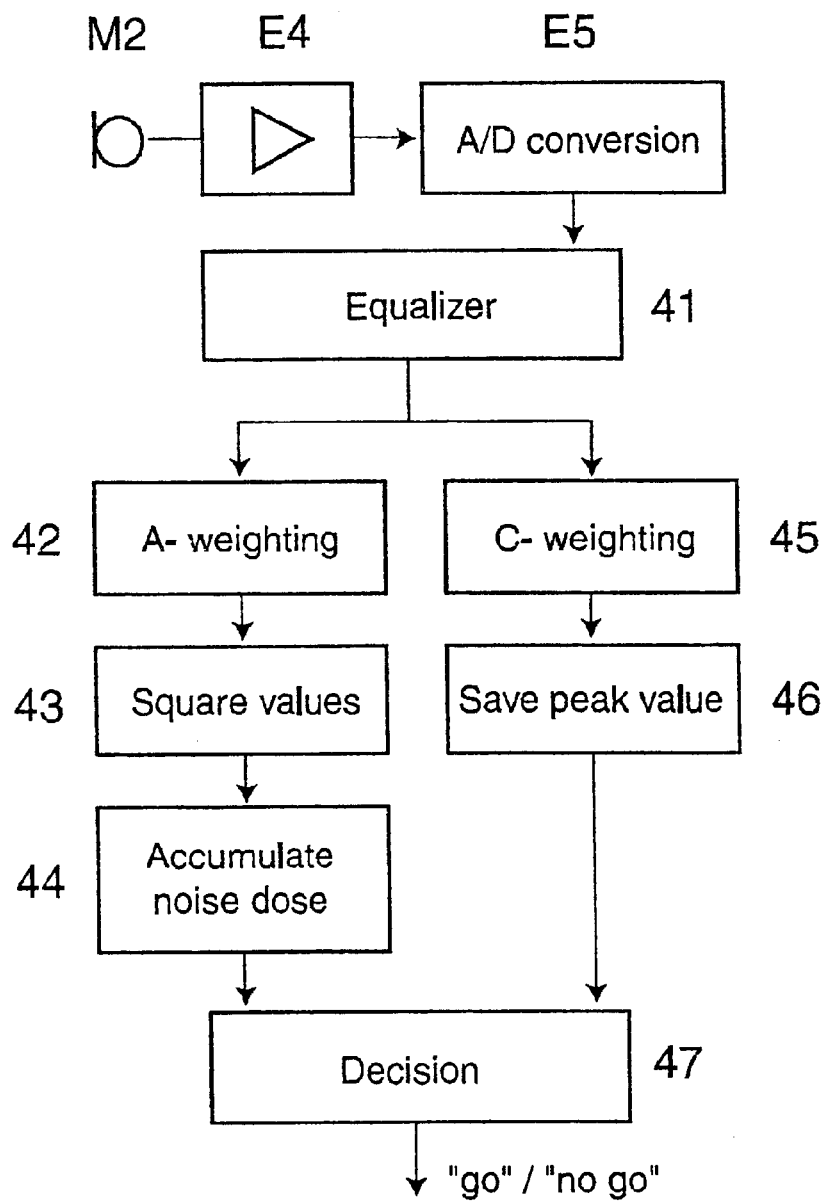
FIG. 7 illustrates a process diagramme for one embodiment of the invention concerning noise dose metering, here illustrating an A-weighting with accumulated noise dose measurements, and also with C-weighting for peak noise value registration.

The signal processing for the computation of noise exposure is shown in the flow diagram in FIG. 7. The signal from microphone M2 is amplified, converted to digital form and analysed by algorithms in processing unit E3. First, sample-by-sample equalization represented by block 41 is applied to compensate for irregularities in the microphone response, the transmission channel T1 and the missing ear canal response due to the blocking of the canal by the earplug. The processed samples may according to the invention be evaluated in at least two ways. To obtain the stationary or semistationary noise dose, an A-weighting represented by block 42 is applied. Standards for this A-weighting exists: IEC 179, and the samples values are squared and accumulated in blocks 43 and 44 respectively. To obtain the peak value for assessing impulsive noise, a C-weighting represented by block 45 is applied according to internationally accepted standards, also IEC 179, and the peak value (regardless of sign) is saved in block 46. The noise dose and peak values are finally compared to predetermined limits in a decision algorithm represented by block 47 so that a warning may be given. The audible information to the user may be provided in form of warning signals or synthetic speech. The warning signal may also be transmitted to other parties, e.g. industrial health care monitoring devices. The time record of the two may also be stored in the memory of the processing unit E3 for later readout and further evaluation.

In addition to the use in passive ear protection devices this embodiment of the invention may be used as ear protection when the terminal is used as a headphone coupled to CD players for similar, monitoring the noise dose submitted from the headphones to the ear over time, or in peaks.

Another embodiment of the invention, called "Online verification/control of hearing protector performance", utilises the fact that a sound field locally generated in the cavity near the eardrum is influenced by leakage in the hearing protector. A small electro-acoustic transducer (sound source) SG and a microphone M2 are arranged in a sealing section 2 arranged for attenuating sounds entering the meatus cavity 3. A digital signal processing (DSP) or microcomputer unit E3 in the main section 1 or in the sealing section 2 is used to generate a predetermined signal which is D/A converted by the D/A converter E7, amplified by amplifier E6 and applied to the sound source SG, which generates a sound field in the closed part of the meatus 3. The microphone M2 picks up the sound in the meatus cavity 3. This signal is amplified by amplifier E4, A/D converted by A/D converter E5, and analysed in the digital signal processor or microprocessor E3. The result of the analysis is compared to stored results from previous measurements of the same type in a situation with good sealing conditions. The user may get audible or other messaged confirmation if the leakage is acceptably low, or a warning signal if leakage is unacceptably high. In the same manner, a signal may be transmitted to other instances, e.g. an external industrial health monitoring unit, with information about the leakage. One example may be that an ear terminal according to the invention is used for checking for leakage in the hearing protection while the wearer is at a gate controlling admittance to a noise exposed area. If leakage occurs, a signal may be transmitted from the ear terminal to a corresponding signal receiver at the gate, having means to block the gate for entrance until the leakage condition is remedied and verified.

FIG. 1 illustrates an embodiment of the invention where the verification device is integrated in a hearing protective earplug. This embodiment comprises an outer section 1 containing a microphone M2 and a sound generator SG. An inner sealing section 2 is attached; to the outer section, but may be made in one integrated outer section/sealing section 1,2. An acoustic transmission channel T2 connects sound generator SG to the inner portion of the meatus 3. The sound generator SG produces a predetermined acoustic signal, which generates a sound field in the meatus 3. An acoustic transmission channel T1 connects microphone M2 to the inner portion of the meatus 3. Microphone M2 picks up the sound field being set up by the sound generator SG. The signal generation and analysis is carried out in a digital signal processing (DSP) or microcomputer unit E3 with appropriate amplifiers and converters as described in the previous paragraphs. All the electronics 11 as well as the power supply 12 are provided in the outer section 1.

Figure 8:
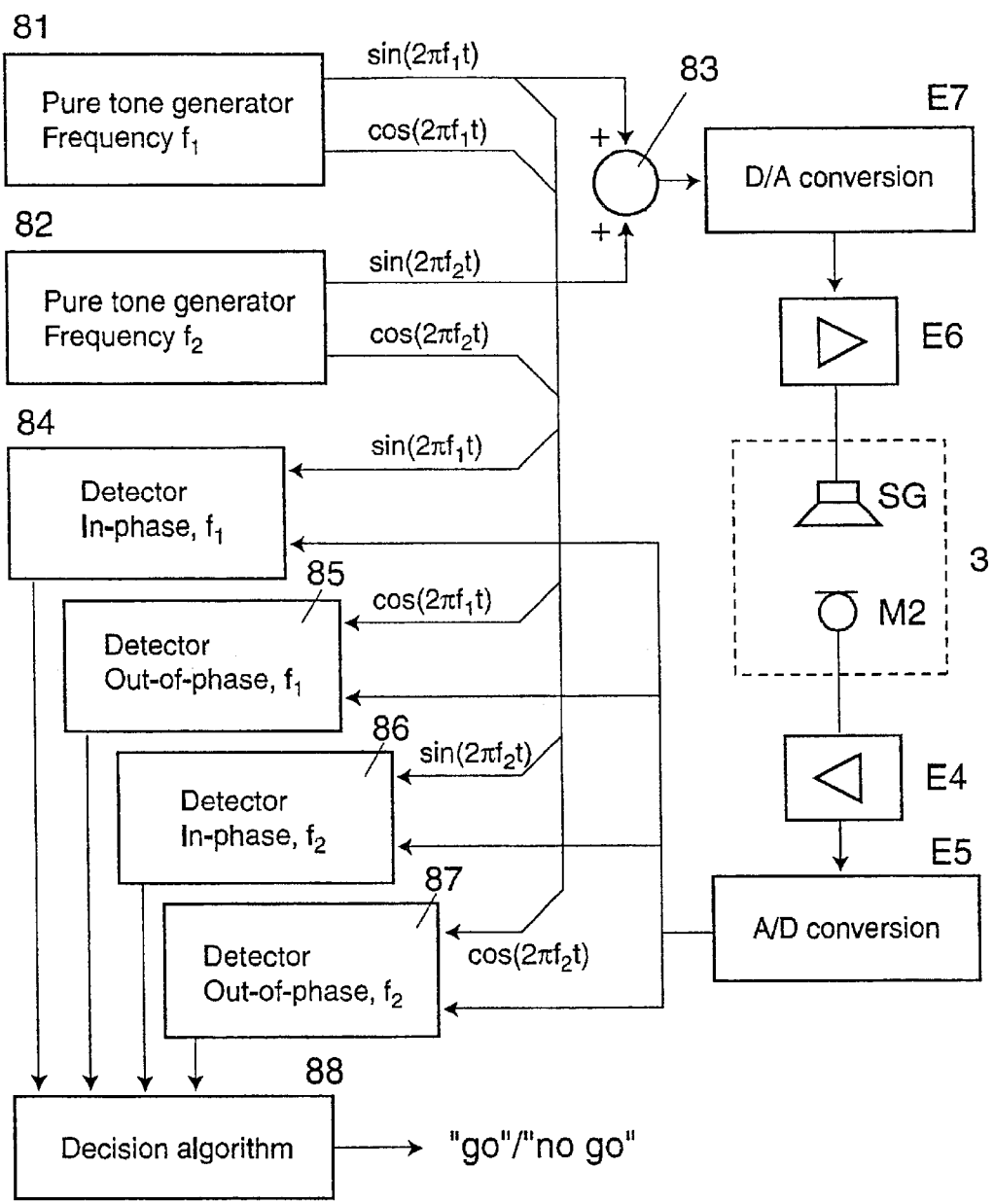
FIG. 8 illustrates another embodiment of the invention illustrating a processing scheme for online verification of hearing protector performance.

FIG. 8 illustrates a signal processing arrangement according to a preferred embodiment of the invention. This embodiment utilises a signal which produces reliable characterisation of the sound field in the cavity, preferably while not being annoying to the user. The signal may comprise one or more sinusoidal components presented simultaneously, or in sequence. Alternatively, a pseudorandom sequence may be employed. In both cases, preferrably both the in-phase and the out-of-phase portions of the sound field are analysed and used in the verification algorithm.

An example of the signal processing is shown in the flow diagram in FIG. 8. In the example, two pure tones of different frequencies $f_1$ and $f_2$ are generated by algorithms in the processing unit E3. The generators are represented by blocks 81 and 82 respectively. The generators generate both the in-phase (sin) and out-of-phase (cos) components. The in-phase components are added together in block 83, converted to analogue form, amplified and applied to the sound generator SG. The resulting sound field is picked up by the microphone M2, amplified, converted to digital form and analysed by algorithms in the processing unit E3 for a series of detectors represented by blocks 84, 85, 86 and 87. The in-phase and out-of-phase components of the microphone M2 signal are analysed for each of the two frequencies. The detector algorithm performs a sample by sample multiplication of the two input signals and smoothes the result with a low-pass filter. The four detector outputs are applied to a decision algorithm represented by block 88 where they are compared to stored values. The decision result may be a digital "go"/"no go" real time signal indicating acceptable noise protection attenuation or unacceptable protection conditions. The result of the analysis is compared to stored results from previous measurements of the same type in a situation with good sealing conditions.

The stored values for the decision algorithm may according to a preferred embodiment be based on previous laboratory experiments, but values for the decision algorithm may also be determined, e.g. making an average and setting a lower acceptance limit for a general-purpose embodiment of the invention.

The number and values of frequencies and the smoothing characteristics of the detectors are chosen as a compromise between audibility and response time. If a continuously running verification should be necessary, low frequencies, e.g. in the range of 10–20 Hz, of sufficiently low levels may be utilised in order to avoid annoyance. The pure tones may then be partially or fully aurally masked by the residual noise transmitted by the hearing protector.

Figure 9:
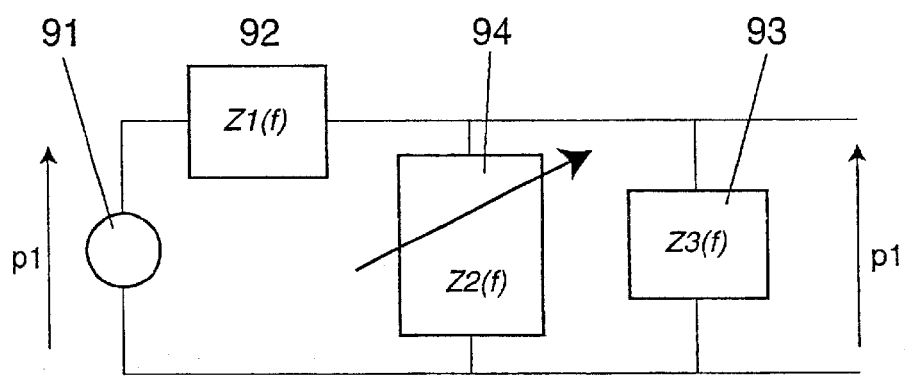
FIG. 9 illustrates an electric analogy diagram of the acoustic phenomenon on which an embodiment for online verification of hearing protector performance is based.

The acoustic phenomenon on which the embodiment of the invention is based is illustrated by the electric analogy diagram in FIG. 9. In the diagram, the sound generator SG is modelled by its acoustic Thevenin equivalent represented by blocks 91 and 92. The sound pressure p1 is generated by the Thevenin generator 91, resulting in a volume velocity through the Thevenin impedance Z1(f) 92. The microphone M2 is modelled by its acoustic impedance Z3(f) represented by block 93. The sound pressure p2 at the microphone entrance is converted to an electric signal by the microphone. For the purpose of the present illustration, all acoustic elements exposed to the sound pressure, generated by the sound generator SG, except the microphone, are lumped together in the acoustic impedance Z2(f) represented by block 95. A leakage in the hearing protector may be modelled by a change in the variable acoustic impedance Z2(f). The change will usually affect both the frequency dependent modulus and the frequency dependent phase of Z2(f). This change leads to a change in the relationship between the sound pressures p2 and p1, which is analysed as described in connection with FIG. 8.

What is claimed is:

1. Ear protecting device comprising:
   a sealing section (2) for acoustically sealing the meatus (3) of a human;
   a sound generator;
   an electronics unit (E3) connected to supply a predetermined signal to the sound generator (SG);
   the sound generator (SG) having a sound outlet ($S_{SG}$) directed toward the user meatus (3) and generating a resulting sound field in the meatus (3) in response to the supplied predetermined signal;
   an inner microphone (M2) with a sound inlet (S2) directed toward the meatus (3), arranged for measuring the resulting sound field in the meatus (3);
   the inner microphone being connected to the electronics unit (11,E3),
   the electronics unit comprising a sound analyser coupled to said inner microphone (M2) for analyzing sound characteristics of the resulting sound field in the meatus (3), and producing analyzed sound characteristics;
   storing unit in the electronics unit (11,E8,E9,E10) providing storage of measured predetermined sound characteristics of a properly functioning ear protecting device;
   a comparing unit in the electronics unit (11,E3) comparing the inner microphone (M2) analyzed sound characteristics with the stored measured predetermined sound characteristics; and
   indicating unit coupled to said comparing unit (11,E3) the indicating unit being activated if said analyzed sound characteristics differ significantly from said predetermined sound characteristics.

2. Ear protecting device according to claim 1, wherein the indicating unit in the electronics unit (11,E3) is arranged to generate a warning signal.

3. Ear protecting device according to claim 2, wherein said indicating unit is arranged for sending said warning signal to said sound generator (SG) for releasing an audible signal to the meatus (3).

4. Ear protecting device according to claim 2, wherein the indicating device comprises a radio link.

5. Ear protecting device according to claim 1, comprising a canal (T1) comprised by the sound inlet (S2), the canal (T1) being arranged through the sealing section (2) between the inward facing surface of the sealing section (2) arranged for sealing off a space portion of the meatus (3), and the sound inlet (S2) of the inner microphone (M2).

6. Ear protecting device according to claim 1, comprising a pressure alignment channel (T3) for slow air throughput to and from the meatus (3) through the sealing section (2).

7. Ear protecting device according to claim 6, wherein the pressure alignment channel (T3) includes a pressure release valve (V).

8. Ear protecting device according to claim 7, comprising a bypass channel (T4) in the pressure alignment channel (T3).

9. Ear protecting device according to claim 1, comprising an outer section (1) arranged for sitting adjacent to the outward facing portion of the sealing section (2) and that part of the inward facing portion of the outer section (1) is formed to fit the concha around the outer portion of the meatus (3).

10. Ear protecting device according to claims 1 comprising a filtering means coupled to said inner microphone for filtering the signal from said inner microphone, and sound generation means for generating sounds based on the filtered signal, said filtering means being preprogrammed to transform the signals based on the sounds received in the ear into a sound being recognized by the user as his own voice.

11. Ear protecting device according to claim 10, wherein the sound generator is positioned in a separate unit being placed in the users other ear.

12. Ear protecting device according to claim 1, comprising analyzing means coupled to said inner microphone (M2) and indicator unit coupled to said analyzing means, said analyzing means analyzing the received sounds and comparing this with predetermined values for acceptable noise levels, and activating said indicating unit when said acceptable noise levels are exceeded.

13. Ear protecting device according to claim 1, comprising
   an outer microphone (M1) for picking up acoustic signals from the space outside of the ear; and
   an electronic unit (11,E3) including filtering means coupled to said inner microphone (M2) for filtering the signal from said inner microphone (M2), said filtering means being programmable to transform the signals based on the sounds received in the ear by said inner microphone (M2) into sounds having essentially the characteristics of spoken sounds of the wearer of the ear protecting device.

14. Ear protecting device according to claim 13, comprising a connection interface (13,E12) for transmitting the filtered signal from the ear protecting device.

* * * * *